United States Patent [19]

Haubrich et al.

[11] Patent Number: 4,861,902
[45] Date of Patent: Aug. 29, 1989

[54] METHOD FOR THE PREPARATION OF TETRAHYDROFURFURYL-(ALPHA)-METHACRYLATE AND CATALYST THEREFOR

[75] Inventors: Gerhard Haubrich, Bonn; Guenter Prescher, Hanau; Juergen Faller, Rodenbach, all of Fed. Rep. of Germany

[73] Assignee: Degussa Aktiengesellschaft, Frankfurt am Main, Fed. Rep. of Germany

[21] Appl. No.: 246,020

[22] Filed: Sep. 16, 1988

Related U.S. Application Data

[63] Continuation of Ser. No. 933,441, Nov. 21, 1986, abandoned.

[30] Foreign Application Priority Data

Dec. 6, 1985 [DE] Fed. Rep. of Germany ....... 3543115

[51] Int. Cl.$^4$ .......................................... C07D 307/08
[52] U.S. Cl. .................................................... 549/499
[58] Field of Search ........................................ 549/499

[56] References Cited

U.S. PATENT DOCUMENTS 2,433,866  1/1948  Rehberg et al. .................... 549/499

FOREIGN PATENT DOCUMENTS 2444033  8/1980  France .
  18293  8/1969  Japan .

OTHER PUBLICATIONS

Rehberg et al, J. Org. Chem., vol. 14 (1949), pp. 1094–1098.

Primary Examiner—Richard L. Raymond
Attorney, Agent, or Firm—Beveridge, DeGrandi & Weilacher

[57] ABSTRACT

A method for the preparation of tetrahydrofurfuryl-(2)-methacrylate by transesterification of methyl methacrylate or ethyl methacrylate with tetrahydrofurfuryl-(2)-methyl alcohol in the presence of the corresponding alkali metal or alkaline earth metal as a catalyst and while air or oxygen is passed through the reaction mixture.

6 Claims, No Drawings

METHOD FOR THE PREPARATION OF TETRAHYDROFURFURYL-(ALPHA)-METHACRYLATE AND CATALYST THEREFOR

This application is a continuation of our application Ser. No. 933,441 filed Nov. 21, 1986, now abnadoned.

The invention pertains to a method for the preparation of tetrahydrofurfurylmethacrylate (THF-MA) by a transesterification reaction of methyl or ethyl methacrylate with tetrahydrofurfuryl alcohol; that is, with tetrahydrofurfuryl-(2)-methyl alcohol (THF-OH).

The production of acrylates and methacrylates of higher alcohols by transesterification of, for example, methyl methacrylate in the presence of alkoxides is known from Japanese patent 19716 (3/31/75). A similar method for producing the corresponding dialkyl amrnoethylesters is shown in Japanese patent 19911 (2/15/79). According to this prior art, however, an alkali metal alkoxide is not to be used as a catalyst.

C. E. Rehberg and W. A. Fanuette describe the production and properties of acrylic and methacrylic esters of alcohols containing ether groups; see J. Org. Chem. 14, 1094–8 (1949). Because these esters are readily polymerized, an oxygen free atmosphere is provided during the reaction. According to this known method a THF-MA yield of 86% is obtained.

In all of the processes kown in accordance with the state of the art, the alcohol that is released in the reaction is distilled off together with small amounts of the initial ester as an azeotrope, thereby shifting the transesterification equilibrium in the desired direction. Despite expensive stabilization measures, the temperatures that are needed in this case lead to losses of yield due to the great tendency of the end product to polymerize. It would be desirable to put an effective stop to the above described polymerization reactions. Since, however, further stabilization measures are ineffective, the reaction conditions must be adjusted to milder conditions.

Therefore, it is an object of the invention to provide a method for the preparation of tetrahydrofurfurylmethacrylate which avoids the problems and difficulties encountered with prior known methods.

In attaining the foregoing object, it is a feature of the invention to carry out a reaction of methyl methacrylate or ethyl methacrylate with tetrahydrofurfuryl-(2)-methyl alcohol in the presence of the tetrahydrofurfuryl-2-methoxide of an alkali metal or an alkaline-earth metal.

Preferably, dried air or pure oxygen is passed through the reaction mixture at the same time during the transesterification reaction, thus improving the yields. The maximum amount of air is 10 ml/hr ×1 (reaction volume).

It is desirable to carry out the transesterification in the presence of stabilizers which are known in the art, such as hydroquinones (e.g. hydroquinone monomethylether), amines such as diphenylamine and phenothiazine, and phenols such as topanol A.

The reaction temperature lies between 45 and 130° C, preferably between 60 and 80° C.

In the preferred aspect of the invention, the catalyst used is the tetrahydrofurfuryl-(2)-methoxide of lithium, magnesium or calcium, which is obtained by reacting Li, $CaH_2$ or Mg with furfuryl alcohol, corresponding to the otherwise well known process for producing alcoholates. Any suitable process for producing alcoholates can be used.

The catalyst is used in the amount of 0.2–10 wt.% and preferably 1–3 wt.%, based on the total weight of the tetrahydrofurfuryl alcohol and methyl methacrylate or ethyl methacrylate used.

The catalysts used in the invention accelerate the reaction to an extraordinary extent and develop their full activity at temperatures between 60 and 80° C.

Space-time yields of up to 2 mol/hr ×1 (relative to the volume of the initial charge) are obtained.

Since the temperatures that are preferably selected are below the boiling point of, for example, the methyl methacrylate/methanol azeotrope, reduced pressures of 300 to 1013 mbar are employed. In order to do this, of course, the stream of air passed through the mixture is calculated in such a way as to prevent the vacuum from collapsing.

Methyl methacrylate or etnyl methacrylate and tetrahydrofurfuryl alcohol are used at a molar ratio of 1.4:1 to 3.0:1, preferably 1.5–2.0:1.

Due to the mild conditions that prevail, the proportion of by-products is reduced to a minimum; the majority of these by-products are polymerizates. This means not only that less initial ester is lost than has been experienced heretofore, but also that a greater product purity is obtained with extractive reprocessing of the sump. Further, because of the low viscosity of the sump, high yields are obtained in the distillative purification step.

The compound produced in accordance with the method of the present invention is a very suitable starting material for the production of polymers.

The invention is further illustrated and described in greater detail in the following examples:

EXAMPLE 1

157 g of THF-OH and 0.26 g of lithium are stirred together at 25–60° C. until a clear solution is obtained. 255.3 g of methylmethacrylate (MMA) and 2.55 g of hydroquinone monomethylether are added thereto, a vacuum of 500 mbar is applied, and the resulting MMA/MeOH azeotrope is distilled of at an overhead temperature of ≦50° C. At a reflux ratio of about 10:1, this process is terminated after 2–2.5 hrs. Excess MMA is now drawn off as a second fraction at 30–50 mbar, and then the reacted alcohol may be taken off as a third fraction. Up till this time, small amounts of dried air are passed through the reaction mixture. A vacuum of 10 mbar is now applied, and the product is taken off at an overhead temperature of 98–100° C. The yield is 231.4 g, the purity (GC) is 96%.

EXAMPLE 2

This experiment is run the same way as in Example 1. The first fraction is taken off in such a way that the sump temperature does not exceed 60° C. To do this, the vacuum is varied between 350 and 250 mbar. At a reflux ratio of 10:1, the removal of the MMA/MeOH azeotrope is terminated after about 3 hours. Reprocessing is done as in Example 1. The yield is 238.2 g, the purity (GC) is 96%.

EXAMPLE 2

164 g of THF-OH and 1.3 g of magnesium are heated with reflux until the evolution of hydrogen can no longer be detected. Then 255.3 g of MMA is added along with 2.55 g of diphenylamine, a vacuum of 600 mbar is applied, and the resulting MMA/MeOH azeotrope is distilled off at an overhead temperature of ≦53° C. (R:E =10:1). Subsequently, the procedure is carried out in the same manner as in Example 1 (air is passed through). The yield is 236 g, the purity (GC) is 95%.

EXAMPLE 4

The procedure is the same as in Example 3, but 2.1 g of $CaH_2$ is used instead of 1.3 g of Mg. Stabilization is done with 2.55 g of topanol A (2,4-dimethyl-6-tert.-butylphenol). The yield is 168 g, the purity (GC) is 96%.

Further variations and modifications of the present invention will be apparent ro those skilled in the art from the foregoing description and are intended to be encompassed by the claims appended hereto.

The German priority application P 35 43 115.6 is relied on and incorporated herein by reference.

We claim:

1. A method for the preparation of tetrahydrofurfuryl-(2)-methacrylate, comprising forming a reaction mixture by reacting methyl or ethyl methacrylate with a sufficient amount of tetrahydrofurfuryl-(2)-methyl alcohol at a temperature of 60 to 80° C. in the presence of a sufficient amount of the tetrahydrofurfuryl-(2)-methoxide of an alkali metal or alkaline-earth metal as a catalyst for the reaction while passing dried air or pure oxygen through the reaction mixture, wherein the molar ratio of said methacrylate to said alcohol is from 1.5 to 2:1 and reacting for a period of time of 2 to 3 hours.

2. The method of claim 1, wherein the reaction proceeds at 45 to 130° C.

3. The method of claim 1, wherein the methoxide of Li, Mg or Ca is used as the catalyst.

4. The method of claim 1, wherein the reaction is carried out at a pressure of 300–1013 mbar.

5. The method of claim 1, further comprising carrying out the reaction in the presence of a stabilizer for the reaction.

6. The method of claim 1, wherein the catalyst is used in the amount of 0.2 to 10 wt.%.

* * * * *